(12) United States Patent
Lu et al.

(10) Patent No.: US 10,871,279 B1
(45) Date of Patent: Dec. 22, 2020

(54) ULTRAVIOLET LED MODULE AND CONTAINER HAVING THE SAME

(71) Applicant: Hergy Lighting Technology Corp., Taipei (TW)

(72) Inventors: Chun-Hung Lu, Taipei (TW); Chia-Te Lin, Taipei (TW)

(73) Assignee: HERGY LIGHTING TECHNOLOGY CORP., Taipei (TW)

( * ) Notice: Subject to any disclaimer, the term of this patent is extended or adjusted under 35 U.S.C. 154(b) by 0 days.

(21) Appl. No.: 16/656,677

(22) Filed: Oct. 18, 2019

(51) Int. Cl.
| | | |
|---|---|---|
| *A61L 9/20* | (2006.01) | |
| *F21V 23/00* | (2015.01) | |
| *F21V 19/00* | (2006.01) | |
| *F21K 9/237* | (2016.01) | |
| *F21K 9/64* | (2016.01) | |
| *F21V 23/02* | (2006.01) | |

(52) U.S. Cl.
CPC ............. *F21V 23/006* (2013.01); *A61L 9/20* (2013.01); *F21K 9/237* (2016.08); *F21K 9/64* (2016.08); *F21V 19/003* (2013.01); *F21V 23/023* (2013.01)

(58) Field of Classification Search
CPC .... F21V 23/006; F21V 23/023; F21V 19/003; A61L 9/20; F21K 9/237
USPC ...................................................... 362/249.2
See application file for complete search history.

(56) References Cited

U.S. PATENT DOCUMENTS

2019/0063695 A1* 2/2019 Oh ............................ F21K 9/69

FOREIGN PATENT DOCUMENTS

| CN | 106186174 A | 12/2016 |
|---|---|---|
| TW | 201721907 A | 6/2017 |
| TW | M560917 U | 6/2018 |

OTHER PUBLICATIONS

Taiwanese Office Action in corresponding Taiwan patent application dated Sep. 26, 2019.

\* cited by examiner

*Primary Examiner* — Karabi Guharay
(74) *Attorney, Agent, or Firm* — Bacon & Thomas, PLLC

(57) ABSTRACT

An ultraviolet LED module and a container having the same are disclosed. The container includes a container cover, a container main body, and an ultraviolet LED module disposed on the container cover. The ultraviolet LED module includes: a case body, having a penetrated hole and not provided with a concave cup; an ultraviolet LED main body, having a LED die exposed in the penetrated hole; a waterproof and dustproof adhesive, filled in a gap between the ultraviolet LED main body and the case body for waterproofing and dustproofing; and an enclosing lens, enclosing the LED die; wherein ultraviolet generated by the LED die emits out from the penetrated hole through the enclosing lens. Accordingly, a power impairment of ultraviolet emitted by the LED die can be as lower as possible.

13 Claims, 6 Drawing Sheets

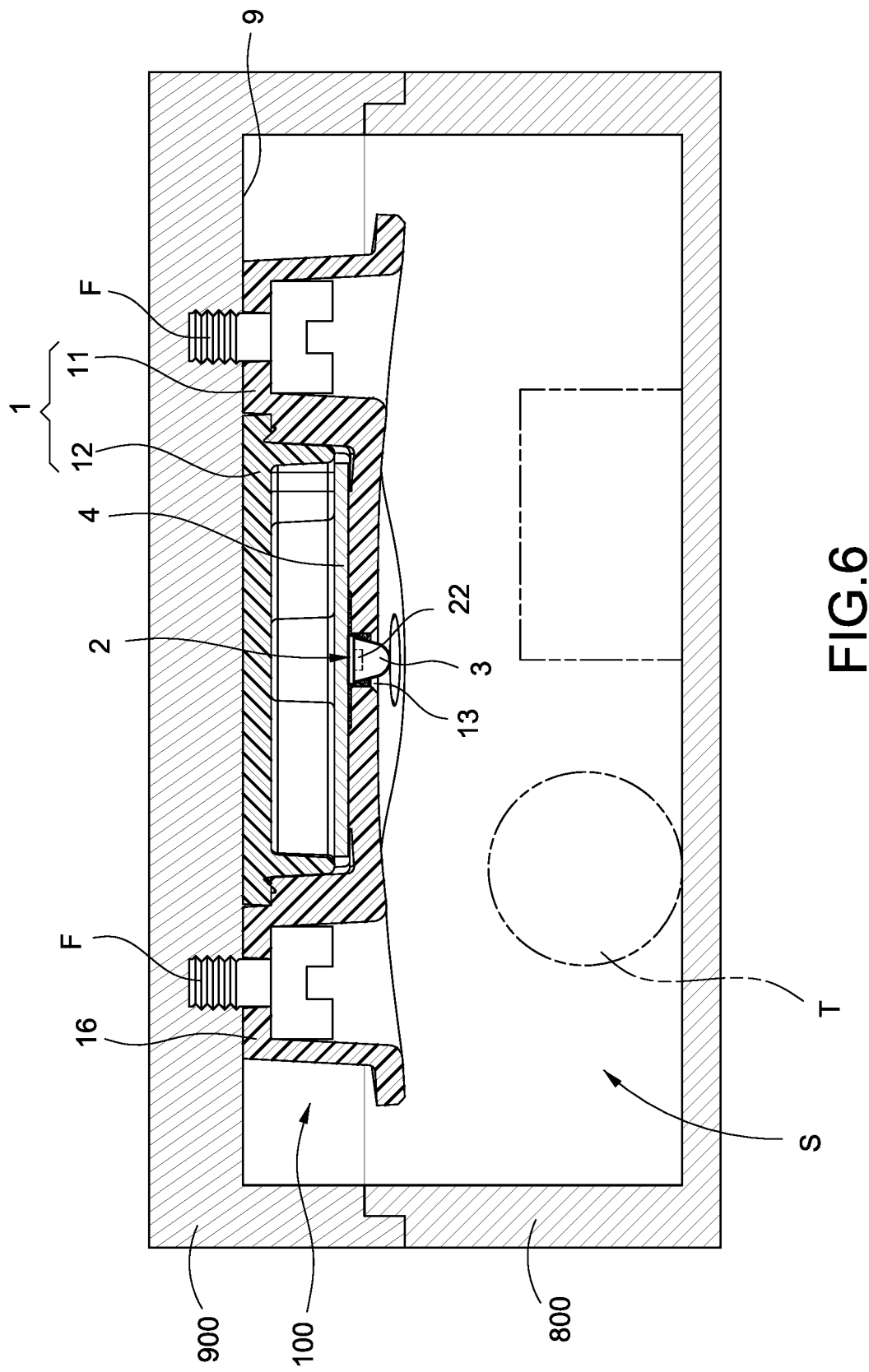

US 10,871,279 B1

ULTRAVIOLET LED MODULE AND CONTAINER HAVING THE SAME

BACKGROUND OF THE INVENTION

Field of the Invention

The present invention relates to an ultraviolet LED, especially to an ultraviolet LED module and a container having the same.

Description of Related Art

An ultraviolet LED (UV LED) is utilized for emitting ultraviolet which is invisible by bare eyes, and for radiating on a target to be radiated, for example drinking water or dining wares for achieving effects of killing germs and sanitizing.

A conventional ultraviolet LED includes a base, a concave cup, an ultraviolet LED main body, a package member and an optical lens. The concave cup is formed on the base, the ultraviolet LED main body is disposed in the concave cup and has a carrier and a LED die, the carrier is disposed on the base, the LED die in disposed on the carrier, the package member is utilized for packing the ultraviolet LED main body in the concave cup, and the optical lens is disposed corresponding to a cup opening of the concave cup. Accordingly, ultraviolet emitted by the LED die is able to radiate to the exterior through the package member, the concave cup and the optical lens.

However, an emitted ultraviolet power of the ultraviolet LED main body is lower than a visible light power emitted by a general LED, and the ultraviolet having the lower power has to be refracted by the package member, reflected by the concave cup and refracted by the optical lens then radiates the exterior, thus the power of the ultraviolet which actually radiates to the exterior has already been impaired, and effects of killing germs and sanitizing could not reach expectations. As such, the above-mentioned disadvantages shall be improved.

SUMMARY OF THE INVENTION

The present invention is to provide an ultraviolet LED module and a container having the same, so that a power impairment of ultraviolet emitted by a LED die can be as lower as possible.

Accordingly, the present invention provides an ultraviolet LED module, which includes: a case body, formed with a penetrated hole, wherein the penetrated hole has an inner circumference; an ultraviolet LED main body, having an outer circumference and including a carrier and a LED die, wherein the carrier is disposed corresponding to the penetrated hole, and the LED die is disposed on the carrier and exposed in the penetrated hole; a waterproof and dustproof adhesive, filled in a gap between the inner circumference and the outer circumference so as to provide a waterproofing and dustproofing effect; and an enclosing lens, enclosing the LED die and capable of altering light pattern of ultraviolet generated by the LED die; wherein, the ultraviolet generated by the LED die is directly radiated from the penetrated hole through the enclosing lens.

Accordingly, the present invention provides a container having ultraviolet LED module, which is used for accommodating a target to be radiated, and includes: a container main body; a container cover, capable of covering the container main body, wherein a storage space for accommodating the target to be radiated is formed between the container cover and the container main body; and an ultraviolet LED module, disposed on the container cover corresponding to the storage space, wherein the ultraviolet LED module includes: a case body, formed with a penetrated hole, wherein the penetrated hole has an inner circumference; an ultraviolet LED main body, having an outer circumference and including a carrier and a LED die, wherein the carrier is disposed corresponding to the penetrated hole, and the LED die is disposed on the carrier and exposed in the penetrated hole; a waterproof and dustproof adhesive, filled in a gap between the inner circumference and the outer circumference so as to provide a waterproofing and dustproofing effect; and an enclosing lens, enclosing the LED die and capable of altering light pattern of ultraviolet generated by the LED die; wherein, the ultraviolet generated by the LED die is directly radiated from the penetrated hole through the enclosing lens to radiate on the target to be radiated.

In comparison with related art, the present invention has advantageous features as follows. The power impairment of the ultraviolet emitted by the LED die can be as lower as possible, thereby ensuring effects of killing germs and sanitizing provided by the ultraviolet LED main body. Moreover, a waterproofing and dustproofing effect is also provided.

BRIEF DESCRIPTION OF DRAWINGS

FIG. 6 is a cross sectional view showing the ultraviolet LED module being applied in a container according to the present invention.

DETAILED DESCRIPTION OF THE INVENTION

Figure 1:
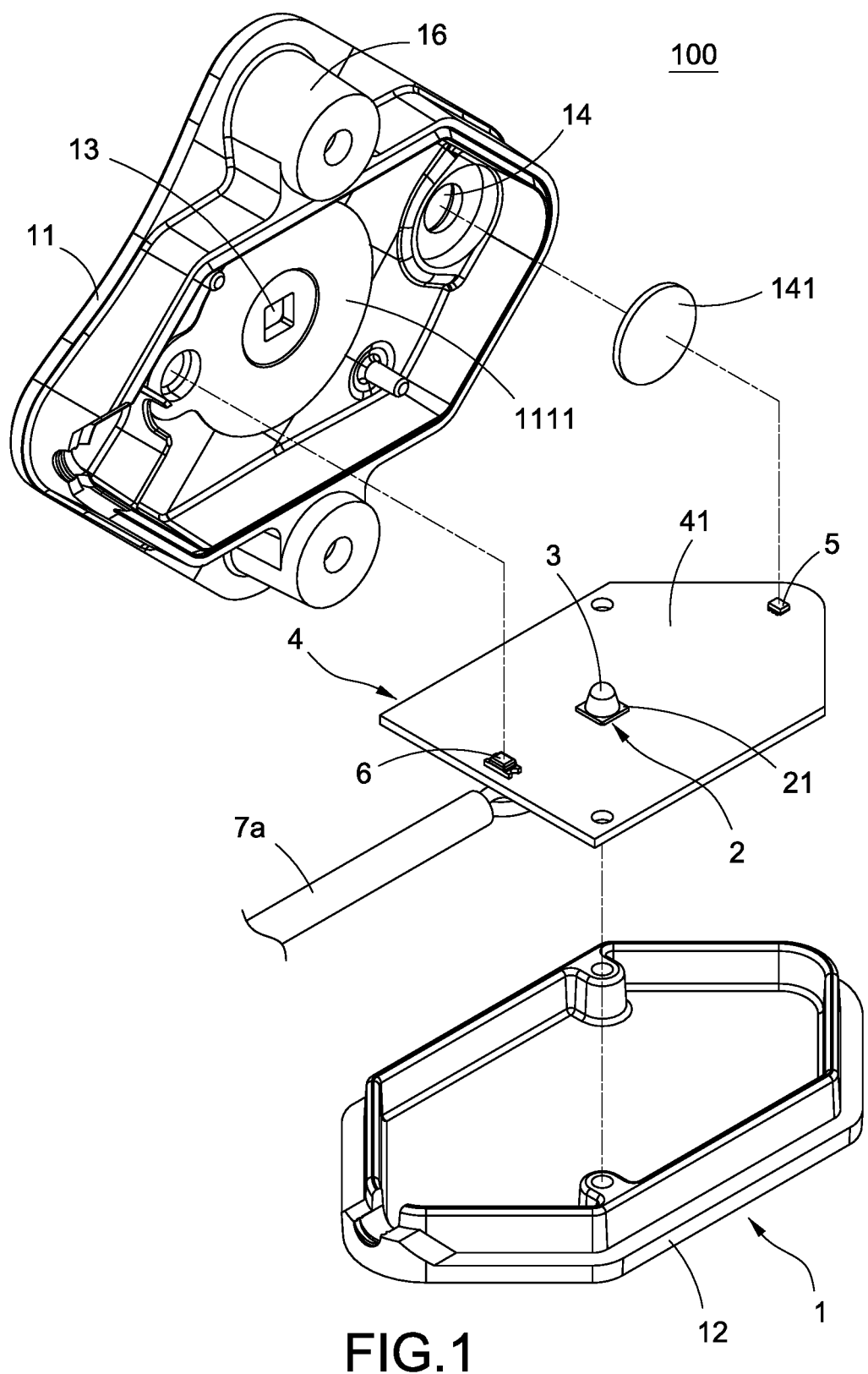
FIG. 1 is a perspective exploded view showing an ultraviolet LED module according to a first embodiment of the present invention.

Preferred embodiments of the present invention will be described with reference to the drawings.

The present invention provides an ultraviolet LED module and a container having the same. A first embodiment of the ultraviolet LED module of the present invention is disclosed with respect from FIG. 1 to FIG. 4, a second embodiment of the ultraviolet LED module of the present invention is disclosed with respect to FIG. 5, and the container having the ultraviolet LED module is disclosed with respect to FIG. 6.

Please refer from FIG. 1 to FIG. 4. According to the first embodiment of the present invention, the LED ultraviolet module 100 includes a case body 1, an ultraviolet LED main body 2 and an enclosing lens 3, and preferably includes a circuit board 4, a light sensing unit 5, an operation indicating unit 6, a power supply unit 7a and a waterproof and dustproof adhesive V1, V2.

The case body 1 has a penetrated hole 13. The case body 1 can be formed as a single-piece structure (not shown in figures); according to this embodiment and as shown in figures, a two-piece structure including a first case member 11 and a second case member 12 is adopted in this embodiment of the present invention, the first case member 11 and the second case member 12 are able to be assembled with each other, and the penetrated hole 13 is formed on the first case member 11.

The ultraviolet LED main body 2 is utilized for emitting ultraviolet, a conventional ultraviolet LED has already included the ultraviolet LED main body 2, and the ultraviolet LED main body 2 includes a carrier 21 and a LED die 22. The carrier 21 is arranged corresponding to the penetrated hole 13, and the LED die 22 is disposed on the carrier 22 and exposed in the penetrated hole 13.

The enclosing lens 3 is utilized for enclosing the LED die 22, and a light pattern altering effect (for example condensing light or diffusing light) is provided after the enclosing lens 3 is disposed. Preferably, the enclosing lens 3 is utilized for enclosing the LED die 22 and fastened on the carrier 21.

Accordingly, a conventional concave cup is not required, the enclosing lens 3 is able to provide two functions of enclosing and altering light pattern, and the ultraviolet LED main body 2 is arranged corresponding to the penetrated hole 13 and the LED die 22 is exposed in the penetrated hole 13, thus ultraviolet generated by the LED die 22 is not affected by the case body 1 and only passes through the enclosing lens 3, the emitted ultraviolet power is only impaired by the enclosing lens 3, so that the ultraviolet emitted by the LED die 22 can be directly radiated from the penetrated hole 13 through the enclosing lens 3, thereby achieving an effect of lowering the impairment of the emitted ultraviolet power.

Figure 4:
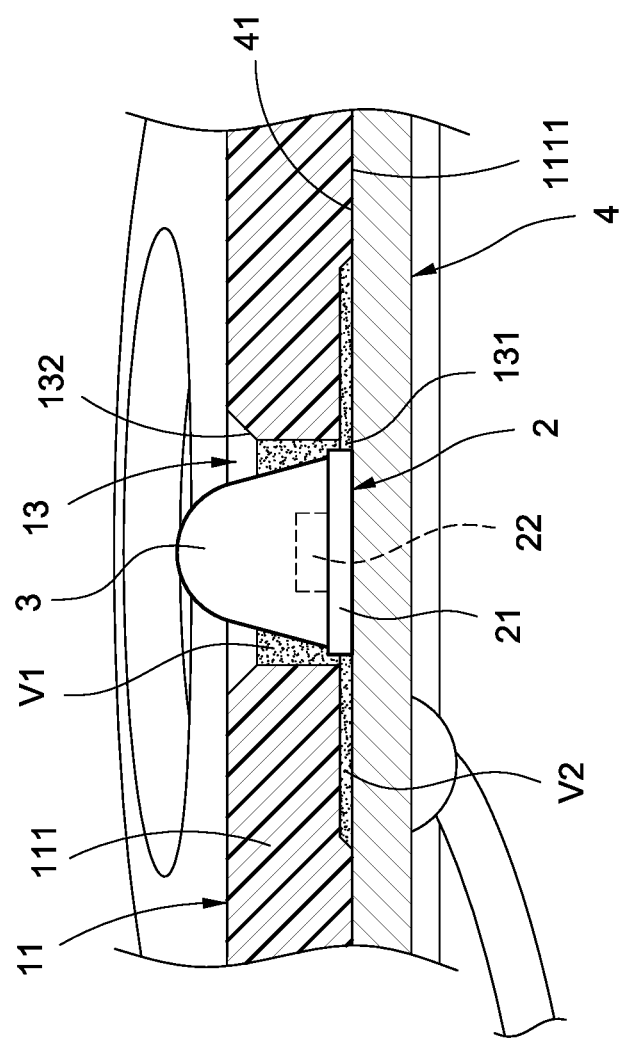
FIG. 4 is a partial enlarged view of FIG. 3 according to the present invention.

The penetrated hole 13 has an inner circumference (not provided with a code), the ultraviolet LED main body 2 has an outer circumference (not provided with a code), a gap between the inner circumference and the outer circumference is filled with the waterproof and dustproof adhesive V1 (as shown in FIG. 4), so that effects of waterproofing and dustproofing and fastening the ultraviolet LED main body 2 and the enclosing lens 3 are both provided.

As shown in FIG. 4, the circuit board 4 is disposed in the case body 1 and has an outer board surface 41, the carrier 21 of the ultraviolet LED main body 2 is disposed on the outer board surface 41; the first case member 11 of the case body 1 has a flat board 111 and is not provided with the conventional concave cup, and the flat board 111 is formed with the penetrated hole 13 and has an inner board surface 1111. What shall be addressed is that the outer board surface 41 of the circuit board 4 is flatly adhered with the inner board surface 1111 of the flat board 111, so that the LED die 22 is able to be located in the penetrated hole 13, and the circuit board 4 and the flat board 111 are stacked with each other for allowing the ultraviolet emitted by the LED die 2 to not be affected by the flat board 111. Preferably, the penetrated hole 13 has an inner end 131 and an outer end 132 which are axially communicated, the carrier 21 is correspondingly disposed at the inner end 131, and the penetrated hole 131 is formed with a conical opening at the outer end 132, thereby reducing any possibility of affecting the ultraviolet.

As shown in FIG. 4, the inner end 131 of the penetrated hole 13 is radially expanded along the inner board surface 1111 of the flat board 111, so that a shallow recess (not provided with a code) is formed relative to the inner board surface 1111, the outer board surface 41 of the circuit board 4 shields the shallow recess so as to form another gap, the another gap is filled with the waterproof and dustproof adhesive V2, and the waterproof and dustproof adhesive V1 and the waterproof and dustproof adhesive V2 are preferably communicated with each other, thereby providing better a better waterproofing and dustproofing effect and a better fastening effect.

A light-pervious hole 14 is formed on the first case member 11 of the case body 1, and the light-pervious hole 14 allows lights to radiate into the case body 1. The light sensing unit 5 is disposed on the outer board surface 41 of the circuit board 4 corresponding to the light-pervious hole 14, so that when lights radiate into the light-pervious hole 14 from an external environment outside the case body 1, the lights are sensed by the light sensing unit 5, and the ultraviolet LED main body 2 can be controlled to be in an OFF status; or the ultraviolet LED main body 2 can be controlled to be in an ON status. Wherein, a light-pervious piece 141 can be disposed in the light-pervious hole 14, the light-pervious piece 141 is provided with effects of light permeating and sealing the light-pervious hole 14, thus a waterproofing and dustproofing effect can be provided after the light-pervious hole 14 is sealed.

The operation indicating unit 6 is disposed on the outer board surface 41 of the circuit board 4, and the operation indicating unit 6 can be in an ON status with the ultraviolet LED main body 2 and be in an OFF status with the ultraviolet LED main body 2, so that an audio and/or optical indication can be provided according to an operating status of the ultraviolet LED main body 2 for allowing a user to clearly know the current operating status of the ultraviolet LED main body 2. According to this embodiment, the operation indicating unit 6 can be a sound generating unit, when the ultraviolet LED main body 2 is controlled to be in the ON status, the operation indicating unit 6 is also in the ON status to generate sounds (for example beep sounds). According to other embodiments which are not shown in figures, the operation indicating unit 6 can also be a light generating unit, so that the operation indicating unit 6 is able to emit lights when the ultraviolet LED main body 2 is in the ON status, and not to emit lights when the ultraviolet LED main body 2 is in the OFF status, and the case body 1 is provided with a light permeating property at a portion thereof corresponding to the operation indicating unit 6.

The power supply unit 7a is disposed on another surface (not provided with a code) of the circuit board 4, the outer board surface 41 and the another surface are arranged to face each other. The power supply unit 7a is utilized for supplying electricity to the ultraviolet LED main body 2; according to this embodiment, the power supply unit 7a is a USB cable, the USB cable is connected between a power source (not shown in figures, and for example public electricity or an electronic product) and the ultraviolet LED module 100 of the present invention, so that the electricity provided by the power source can be supplied to the ultraviolet LED module 100 via the USB cable.

Figure 5:
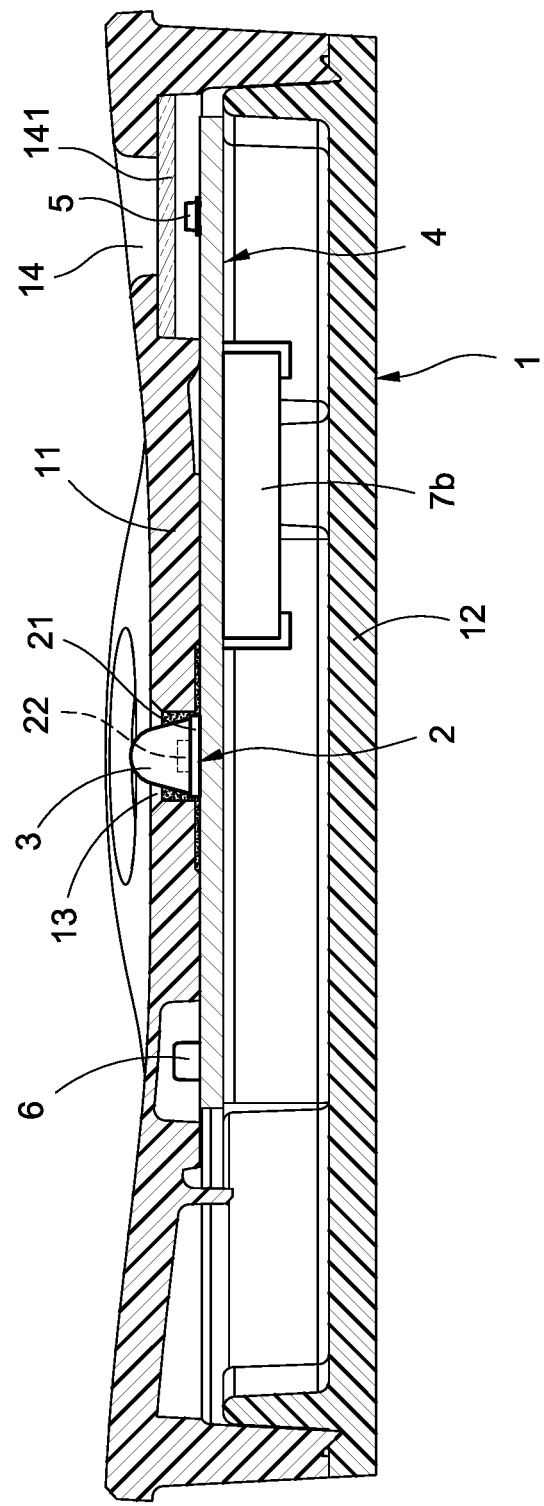
FIG. 5 is a cross sectional view showing the ultraviolet LED module according to a second embodiment of the present invention.

Please refer to FIG. 5, which discloses the second embodiment of the ultraviolet LED module 100 of the present invention, the second embodiment is substantially the same as the first embodiment, a difference between the second embodiment and the first embodiment is that a battery is adopted as a power supply unit 7b according to the second embodiment.

Please refer to FIG. 6, which discloses the container having the ultraviolet LED module 100 of the present invention, the container can be an environmental-friendly meal box or a pitcher, but what shall be addressed is that the scope of the present invention is not limited to the above-mentioned container, the container can be any container in which an stored target requires the radiation of ultraviolet.

As show in FIG. 6, the container includes: a container main body 800, a container cover 900 and the aforesaid ultraviolet LED module 100. Wherein, the container cover 900 is utilized for covering the container main body 800, a storage space S is formed after the container cover 900 covers the container main body 800, and a target to be radiated T can be accommodated in the storage space S. The ultraviolet LED module 100 is disposed on the container cover 900 corresponding to the storage space S, so that the ultraviolet LED module 100 is able to radiate the ultraviolet to the target to be radiated T.

Accordingly, when the container main body 800 is covered by the container cover 900, external lights are blocked by the container and the light sensing unit 5 is unable to sense the lights, thus the ultraviolet LED main body 2 is controlled to be in the ON status for radiating the ultraviolet to the target to be radiated T; on the other hands, when the container cover 900 is opened, the light sensing unit 5 is able to sense the external lights, thus the ultraviolet LED main body 2 is in the OFF status, thereby stopping the ultraviolet from radiating to the target to be radiated T.

Figure 2:
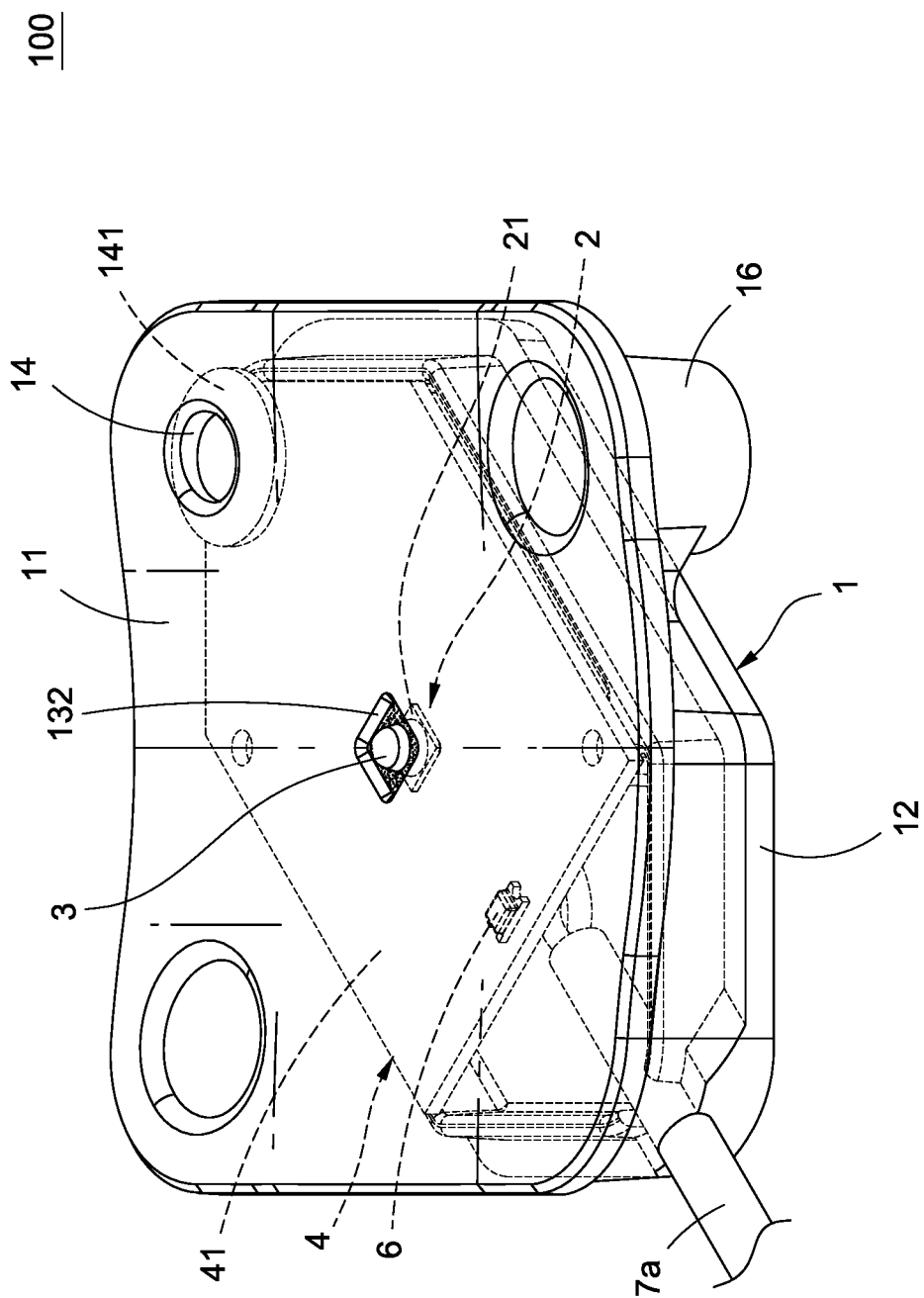
FIG. 2 is a perspective view showing the assembly of the ultraviolet LED module according to the first embodiment of the present invention.
Figure 3:
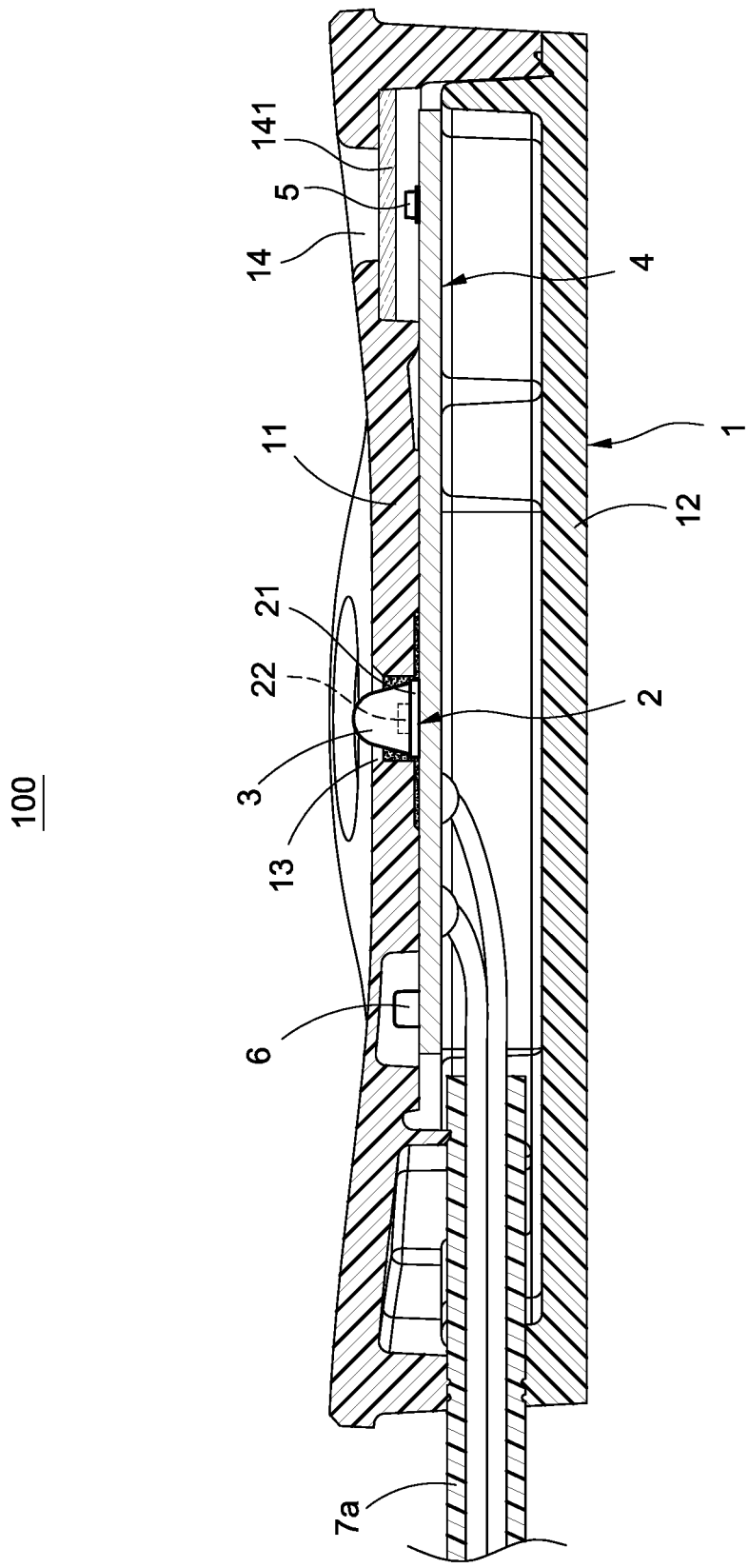
FIG. 3 is a cross sectional view showing the ultraviolet LED module according to the first embodiment of the present invention.

Preferably, the container cover 900 has an inner top cover surface 9, the first case member 11 of the ultraviolet LED module 100 has a plurality of fasten parts 16, each of the fasten parts 16 is located out of the second case member 12 (as shown in FIG. 2). A plurality of fasten units F are served to fasten the ultraviolet LED module 100 on the inner top cover surface 9 via each of the fasten parts 16, and an emitting direction of the LED die 22 is mostly towards the target to be radiated T.

Moreover, the light sensing unit 5 cannot only be the above-mentioned sensing unit utilized for sensing the environmental lights, the light sensing unit 5 can also be a sensing unit utilized for sensing the ultraviolet. When the sensing unit utilized for sensing the ultraviolet is adopted as the light sensing unit 5, the ultraviolet emitted by the ultraviolet LED main body 2 can be sensed. For example, the illuminance of the ultraviolet emitted by the ultraviolet LED main body 2 can be designed to be continuously or intermittently sensed, and the illuminance of the ultraviolet sensed by the light sensing unit 5 can be sent to a control panel (not shown in figures) for monitoring by utilizing a transmission cable (not shown in figures) connected between the circuit board 4 and the control panel.

Furthermore, it also can be set that when the sensed illuminance of the ultraviolet deteriorates to a set range or deteriorates to a certain ratio, the operation indicating unit 6 can be controlled to generate audio or optical warnings to inform the user that the performance of the ultraviolet LED module 100 of the present invention has deteriorated to a certain level, and the functions of killing germs and sanitizing cannot be sufficiently provided.

Furthermore, when the light sensing unit 5 senses the illuminance of the ultraviolet continuously decreases, the control panel is able to send a light adjusting signal to the circuit board 4 to increase a current via the transmission cable, so that the required illuminance of the ultraviolet can be complemented. The circuit board 4 can also be set to detect that when the illuminance of the ultraviolet decreases, the current can be directly increased for complementing the required illuminance of the ultraviolet, Moreover, when the current exceeds an upper limit of the ultraviolet LED main body 2, the circuit board 4 is able to send a malfunction signal to be control panel, or the power can be directly terminated via the circuit board 4, and the operation indicating unit 6 is controlled to provide the audio or optical warnings to inform the user that the ultraviolet LED module 100 has been in a malfunction status.

Based on what has been disclosed above, the ultraviolet LED module and the container having the same provided by the present invention is novel and more practical in use comparing to prior arts.

Although the present invention has been described with reference to the foregoing preferred embodiment, it will be understood that the invention is not limited to the details thereof. Various equivalent variations and modifications can still occur to those skilled in this art in view of the teachings of the present invention. Thus, all such variations and equivalent modifications are also embraced within the scope of the invention as defined in the appended claims.

What is claimed is:

1. An ultraviolet LED module, comprising:
a case body, formed with a penetrated hole, wherein the penetrated hole has an inner circumference;
an ultraviolet LED main body, having an outer circumference and including a carrier and a LED die, wherein the carrier is disposed corresponding to the penetrated hole, and the LED die is disposed on the carrier and exposed in the penetrated hole;
a waterproof and dustproof adhesive, filled in a gap between the inner circumference and the outer circumference so as to provide a waterproofing and dustproofing effect;
an enclosing lens, enclosing the LED die and capable of altering light pattern of ultraviolet generated by the LED die;
a circuit board, disposed in the case body, and having an outer board surface; and
a light sensing unit, disposed on the outer board surface of the circuit board corresponding to a light pervious hole formed on the case body;
wherein, the ultraviolet generated by the LED die is directly radiated from the penetrated hole through the enclosing lens, the carrier is disposed on the outer board surface, the case body has a flat board, the flat board is formed with the penetrated hole and has an inner board surface, the outer board surface of the circuit board is flatly adhered with the inner board surface of the flat board, the ultraviolet LED main body is controlled to be in an ON status when no light is sensed by the light sensing unit, and the ultraviolet LED main body is controlled to be in an OFF status when lights are sensed by the light sensing unit.

2. The ultraviolet LED module according to claim 1, wherein the penetrated hole has an inner end and an outer end, the carrier is correspondingly disposed at the inner end, and the penetrated hole is formed with a conical opening at the outer end.

3. The ultraviolet LED module according to claim 1, further including an operation indicating unit, wherein the operation indicating unit is disposed on the outer board surface of the circuit board, and the operation indicating unit is in an ON status with the ultraviolet LED main body and in an OFF status with the ultraviolet LED main body.

4. The ultraviolet LED module according to claim 1, further including a power supply unit, wherein the power supply unit is disposed on another surface, which is opposite to the outer board surface, of the circuit board, and utilized for supplying electricity to the ultraviolet LED main body.

5. The ultraviolet LED module according to claim 4, wherein the power supply unit is a battery or a USB cable.

6. The ultraviolet LED module according to claim 1, further including a light sensing unit and an operation indicating unit, wherein a light-pervious hole is formed on the case body, the light sensing unit is disposed on the outer board surface of the circuit board corresponding to the light-pervious hole, the operation indicating unit is disposed on the outer board surface of the circuit board, and the light sensing unit senses an illuminance of the ultraviolet generated by the LED die and the operation indicating unit is able to provide indications or warnings.

7. A container having ultraviolet LED module, used for accommodating a target to be radiated, and comprising:
 a container main body;
 a container cover, capable of covering the container main body, wherein a storage space for accommodating the target to be radiated is formed between the container cover and the container main body; and
 an ultraviolet LED module, disposed on the container cover corresponding to the storage space and including:
  a case body, formed with a penetrated hole, wherein the penetrated hole has an inner circumference;
   an ultraviolet LED main body, having an outer circumference and including a carrier and a LED die, wherein the carrier is disposed corresponding to the penetrated hole, and the LED die is disposed on the carrier and exposed in the penetrated hole;
   a waterproof and dustproof adhesive, filled in a gap between the inner circumference and the outer circumference so as to provide a waterproofing and dustproofing effect; and
   an enclosing lens, enclosing the LED die and capable of altering light pattern of ultraviolet generated by the LED die;
  wherein, the ultraviolet generated by the LED die is directly radiated from the penetrated hole through the enclosing lens to radiate on the target to be radiated, the ultraviolet LED module includes a circuit board, the circuit board is disposed in the case body and has an outer board surface, the carrier is disposed on the outer board surface, the case body has a flat board, the flat board is formed with the penetrated hole and has an inner board surface, the outer board surface of the circuit board is flatly adhered with the inner board surface of the flat board, the ultraviolet LED module includes a light sensing unit, a light-pervious hole is formed on the case body, the light sensing unit is disposed on the outer board surface of the circuit board corresponding to the light-pervious hole, the ultraviolet LED main body is controlled to be in an ON status when no light is sensed by the light sensing unit, and the ultraviolet LED main body is controlled to be in an OFF status when lights are sensed by the light sensing unit.

8. The container according to claim 7, wherein the container cover has an inner top cover surface, the case body of the ultraviolet LED module has a plurality of fasten parts, and a plurality of fasten units are served to fasten the ultraviolet LED module on the inner top cover surface via the plurality of fasten parts.

9. The container according to claim 7, wherein the penetrated hole of the case body has an inner end and an outer end, the carrier is correspondingly disposed at the inner end, and the penetrated hole is formed with a conical opening at the outer end.

10. The container according to claim 7, wherein the ultraviolet LED module includes an operation indicating unit, the operation indicating unit is disposed on the outer board surface of the circuit board, and the operation indicating unit is in an ON status with the ultraviolet LED main body and in an OFF status with the ultraviolet LED main body.

11. The container according to claim 7, wherein the ultraviolet LED module includes a power supply unit, the power supply unit is disposed on another surface, which is opposite to the outer board surface, of the circuit board, and utilized for supplying electricity to the ultraviolet LED main body.

12. The container according to claim 11, wherein the power supply unit is a battery or a USB cable.

13. A container having ultraviolet LED module, used for accommodating a target to be radiated, and comprising:
 a container main body;
 a container cover, capable of covering the container main body, wherein a storage space for accommodating the target to be radiated is formed between the container cover and the container main body; and
 an ultraviolet LED module, disposed on the container cover corresponding to the storage space and including:
  a case body, formed with a penetrated hole, wherein the penetrated hole has an inner circumference;
   an ultraviolet LED main body, having an outer circumference and including a carrier and a LED die, wherein the carrier is disposed corresponding to the penetrated hole, and the LED die is disposed on the carrier and exposed in the penetrated hole;
   a waterproof and dustproof adhesive, filled in a gap between the inner circumference and the outer circumference so as to provide a waterproofing and dustproofing effect; and
   an enclosing lens, enclosing the LED die and capable of altering light pattern of ultraviolet generated by the LED die;
  wherein, the ultraviolet generated by the LED die is directly radiated from the penetrated hole through the enclosing lens to radiate on the target to be radiated, the ultraviolet LED module includes a circuit board, the circuit board is disposed in the case body and has an outer board surface, the carrier is disposed on the outer board surface, the case body has a flat board, the flat board is formed with the penetrated hole and has an inner board surface, the outer board surface of the circuit board is flatly adhered with the inner board surface of the flat board, the ultraviolet LED module includes a light sensing unit and an operation indicating unit, a light-pervious hole is formed on the case body, the light sensing unit is disposed on the outer board surface of the circuit board corresponding to the light-pervious hole, the operation indicating unit is disposed on the outer board surface of the circuit board, and the light sensing unit senses an illuminance of the ultraviolet generated by the LED die and the operation indicating unit is able to provide indications or warnings.

* * * * *